(12) United States Patent
Brandenburger et al.

(10) Patent No.: US 7,857,802 B2
(45) Date of Patent: Dec. 28, 2010

(54) CONNECTOR FOR MEDICAL LIQUID-CONTAINING PACKAGES AND MEDICAL LIQUID-CONTAINING PACKAGES

(75) Inventors: Torsten Brandenburger, Niddatal (DE); Ismael Rahimy, Friedberg (DE)

(73) Assignee: Fresenius Kabi Deutschland GmbH, Bad Homburg V.D.H. (DE)

( * ) Notice: Subject to any disclaimer, the term of this patent is extended or adjusted under 35 U.S.C. 154(b) by 774 days.

(21) Appl. No.: 10/575,690

(22) PCT Filed: Oct. 15, 2004

(86) PCT No.: PCT/EP2004/011603

§ 371 (c)(1), (2), (4) Date: Aug. 23, 2006

(87) PCT Pub. No.: WO2005/037362

PCT Pub. Date: Apr. 28, 2005

(65) Prior Publication Data

US 2007/0060902 A1 Mar. 15, 2007

(30) Foreign Application Priority Data

Oct. 15, 2003 (DE) .......................... 103 48 016

(51) Int. Cl.
*A61B 19/00* (2006.01)

(52) U.S. Cl. .................. 604/415; 604/408; 604/256

(58) Field of Classification Search .................. 604/403, 604/408, 415
See application file for complete search history.

(56) References Cited

U.S. PATENT DOCUMENTS 5,088,995 A 2/1992 Schnell et al.
5,100,394 A * 3/1992 Dudar et al. ................ 604/537
6,142,446 A 11/2000 Leinsing
6,183,448 B1 2/2001 Mayer
6,186,997 B1 2/2001 Gabbard et al.
6,325,782 B1 12/2001 Lopez
6,364,143 B1 4/2002 Knierbein (Continued)

FOREIGN PATENT DOCUMENTS

CN 2276810 Y 3/1998

(Continued)

OTHER PUBLICATIONS

Translation of First Office Action in related Chinese Application No. 200480030631.2, 4 pages (date of publication not available).

*Primary Examiner*—Leslie R Deak
(74) *Attorney, Agent, or Firm*—Hamilton, Brook, Smith & Reynolds, P.C.

(57) ABSTRACT

The invention relates to a connector for medical liquid-containing packages, in particular to infusion or transfusion bags comprising a connection element (1) provided with a channel-shaped opening (1c) in which a self-sealing membrane (8) is arranged. A breakable part (17) which is connected to the connection piece closes the channel-shaped opening. Above the membrane (8), said connection element is embodied in the form a connection piece (13) comprising an internal cone (14) and external thread (15), the membrane (8) being sealed for receiving a syringe cone shaft. The inventive connector makes it possible to inject an active substance by means of a conventional Luer lock syringe devoid of an injection cannula (needle).

17 Claims, 4 Drawing Sheets

U.S. PATENT DOCUMENTS

Figure 3:
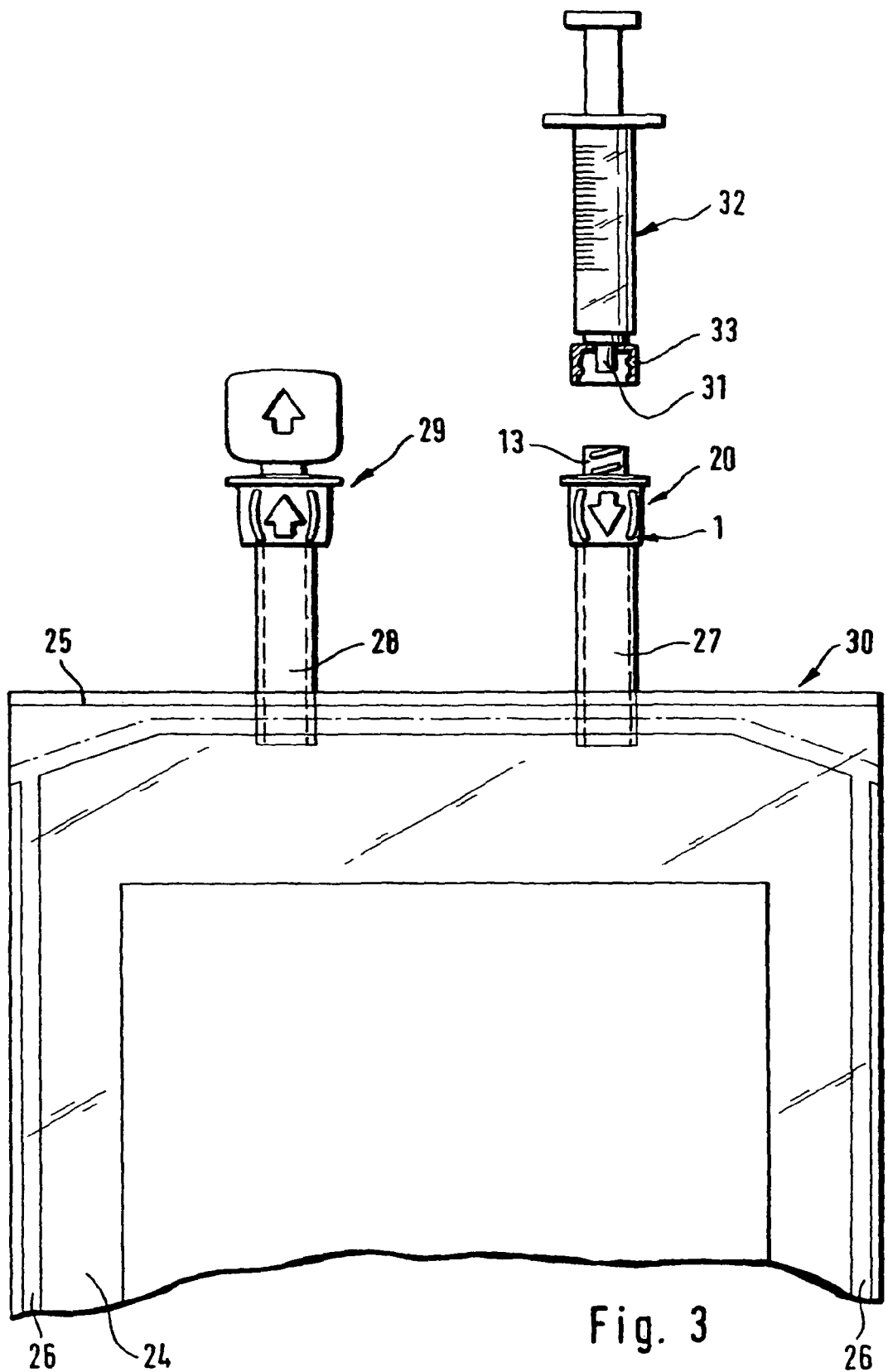

2003/0199835 A1 * 10/2003 Leinsing et al. ............. 604/256
2005/0215943 A1     9/2005 Brandenburger et al.

FOREIGN PATENT DOCUMENTS

| DE | 196 36 610 C2 | 7/1997 |
| DE | 197 28 775 C2 | 1/1999 |
| DE | 100 30 474 C1 | 2/2002 |
| WO | WO 96/23545 A | 8/1996 |
| WO | WO 2004/084793 A | 10/2004 |

* cited by examiner

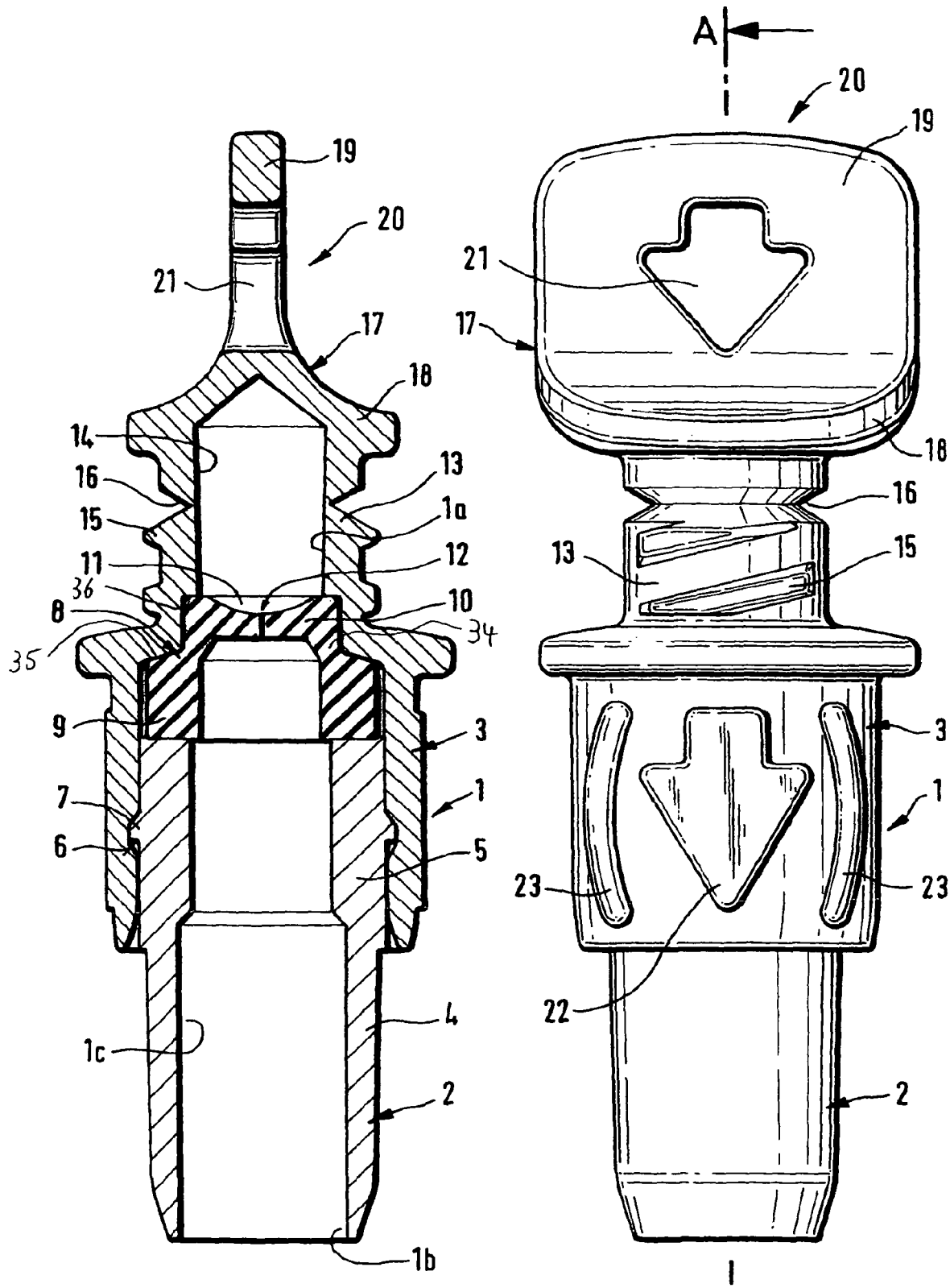

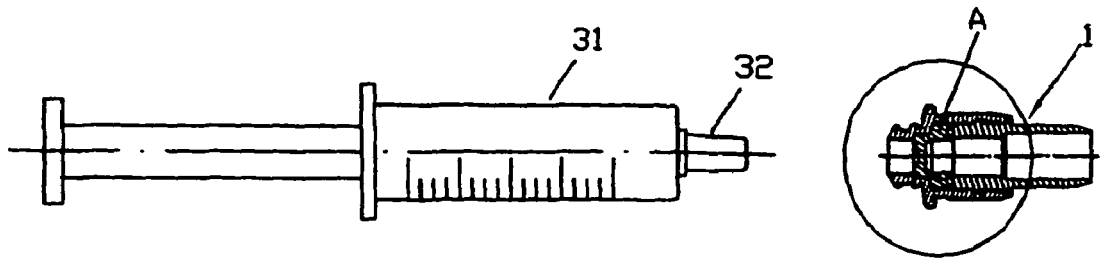
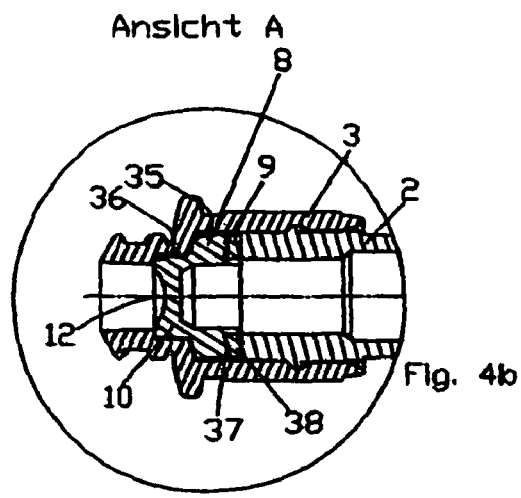
Ansicht A
Fig. 4b
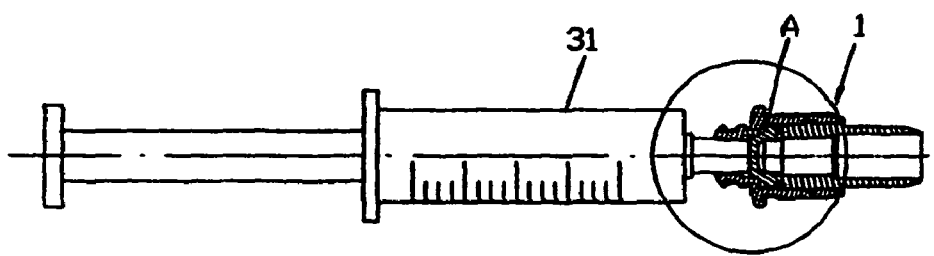
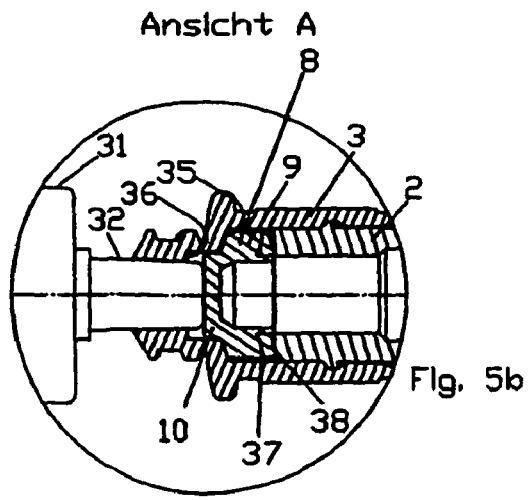
Ansicht A
Fig. 5b

Ansicht A

US 7,857,802 B2

CONNECTOR FOR MEDICAL LIQUID-CONTAINING PACKAGES AND MEDICAL LIQUID-CONTAINING PACKAGES

RELATED APPLICATIONS

This application is the U.S. National Stage of International Application No. PCT/EP2004/011603, filed Oct. 15, 2004, published in German, and claims priority under 35 U.S.C. §119 or 365 to German Application No. 103 48 016.1, filed Oct. 15, 2003.

The invention relates to a connector for medical liquid-containing packages, in particular infusion and transfusion bags, said connector being used for the injection of a liquid into the bag. Moreover, the invention relates to a medical liquid-containing package, in particular an infusion or transfusion bag, with such an injection part.

An infusion bag with an injection part and an extraction part is known from WO 96/23545. The injection part is used to supply a drug by means of an injection syringe which has a thin cannula (needle). It includes a tubular connection part, which is closed by a protective cap formed as a break-off part. A self-sealing septum sits in the opening area of the connection part. A pierceable membrane in the connection part prevents the septum from coming into contact with the solution before the use of the infusion bag. The extraction part, which is used for the extraction of the solution by means of a spike, has a self-sealing septum.

The known injection parts are characterised in that the self-sealing septum is arranged in the opening area of the tubular connection part, in such a way that it ends essentially flush with the connection part. After the breaking-off of the break-off part, the septum lies free. The septum is pierced by an injection needle for the injection of a drug. Such injection parts are also known for example from DE 197 28 775 A1 and DE 100 30 474 C1.

The known injection parts have been tried and tested in practice. Drawbacks do however arise from the use of an injection needle for the injection of an active substance. On the one hand, there is the risk of the connection between the injection needle and the septum becoming loose due to an unintended tug on the syringe or an excess pressure in the interior of the bag. On the other hand, there is an increased risk of injury to the nursing staff due to the injection needle. The package can also be damaged by the needle if it is not handled properly. The supply of a viscous active substance, moreover, is made difficult on account of the small cross-section of the injection needle. The supply of a highly fluid active substance takes a relatively long time on account of the small cross-section.

Conical connections with a conical shaft and a conical sleeve, whose conical surfaces are standardised, are known in medical technology for the connection of medical devices. The non-lockable conical connections with standardised conical surfaces are referred to as Luer connectors and the lockable conical connections as Luer lock connectors. The Luer connectors or Luer-lock connectors with a conical shaft are referred to as male connectors and the connectors with a conical sleeve as female connectors.

DE 196 36 610 A1 describes a filling device for a supply system for active substances, which is connected via a line to a system reservoir. The active substance is fed to the filling device by means of a conventional syringe without an injection needle. The connection of the syringe to the filling device takes place via a Luer lock connection.

There is known from WO 00/02517 a sterile connector for the connection of the spike of a transfer device, which has a base part with a channel-shaped recess which is closed by a break-off part. The base part has a mounting piece for the spike, said mounting piece being formed essentially cylindrically. The known connector is neither intended nor suitable for the connection of a Luer lock syringe.

U.S. Pat. No. 6,186,997 describes an infusion bag with a tube piece, which is closed at the end with a slit membrane. A closure cap is screwed with the end piece of the tube piece.

The problem underlying the invention is to provide a connector for medical liquid-containing packages, in particular infusion and transfusion bags, which connector is able to be produced cost-effectively and handled in a straightforward and safe manner and permits a rapid supply of, in particular, a viscous active substance, and with which the risk of injury to the nursing staff and damage to the package is low.

A further problem of the invention is to provide a package for medical liquids, in particular infusion and transfusion bags, which package is able to be handled in a straightforward and safe manner and into which package viscous active substances can also be rapidly injected without risk of injury to the nursing staff or damage to the package.

According to the invention, the solution to the aforementioned problems takes place with the features of claims 1 and 17. Advantageous embodiments of the invention are the subject-matter of the sub-claims.

The connector according to the invention permits the connection of a conventional syringe to a conical connection, in particular a Luer conical connection or a Luer lock conical connection, which does not have an injection needle. Since an injection needle with a small cross-section is not required, active substances of greater viscosity can also be injected rapidly. The risk of injury to nursing staff and damage to the package does not exist. The possibility of screwing the syringe and the connector ensures that the connection does not become detached. The connector has a self-sealing slit membrane, which is arranged beneath the upper opening on the connection side. Above the self-sealing membrane, the connection part of the connector is designed as a connection piece with an internal cone for the conical shaft of the syringe. The self-sealing membrane is slit in a continuous manner so as to receive the conical shaft of the syringe in a sealing fashion. After the withdrawal of the conical shaft, the membrane closes again and thus prevents the liquid from running out of the package.

An advantageous embodiment of the invention makes provision such that the break-off part is connected via an annular rupture zone to the connection part, so that the break-off part has a secure hold, but is nonetheless detached relatively easily.

In a particularly preferred embodiment, the connection part comprises a lower section and an upper section, whereby the sections are fixed in a snap-in fashion. The self-sealing membrane is preferably held clamped between the lower and the upper section. The assembly is thus simplified. The connection part can however also be in one piece.

The self-sealing membrane preferably has a lower annular portion and upper plate-shaped portion. The annular portion of the membrane is preferably clamped between the upper and lower section of the connection part. The membrane thus has a more secure hold. The upper plate-shaped portion of the membrane preferably has a trough-shaped recess. The trough-shaped recess on the one hand ensures that the conical shaft of the syringe is guided reliably and on the other hand guarantees that the membrane provides a reliable seal after the conical shaft has been withdrawn. It has been shown in tests that the special design of the membrane is decisive for the immediate re-sealing, whereby the sealing of the membrane is increased still further with increasing internal pressure in the package.

The upper plate-shaped portion of the self-sealing membrane is preferably followed by a middle intermediate piece, which transforms into the lower annular portion of the membrane. The upper and lower portion of the membrane are connected together elastically, so that the membrane is deformed when the conical shaft of the syringe is introduced, in such a way that it provides a more reliable seal with respect to the connection part.

The inner diameter of the annular portion of the self-sealing membrane is preferably smaller than the inner diameter of the channel-shaped recess of the connection part. It has been shown that the re-sealing of the membrane is thus further improved.

The internal cone of the connection piece and the self-sealing membrane of the connection part are, furthermore, preferably designed and arranged in such a way that the conical shaft of the syringe inserted into the internal cone opens the slit membrane, but does not penetrate it.

The break-off part of the connector is preferably designed as a flat grip, so that it can be held with the thumb and forefinger. Handling is thus simplified.

It is expedient for the connector to be an injection-moulded apart, which can be produced cost-effectively in large numbers.

An example of embodiment of the invention is explained below in greater detail by reference to the drawings.

Figure 6A:
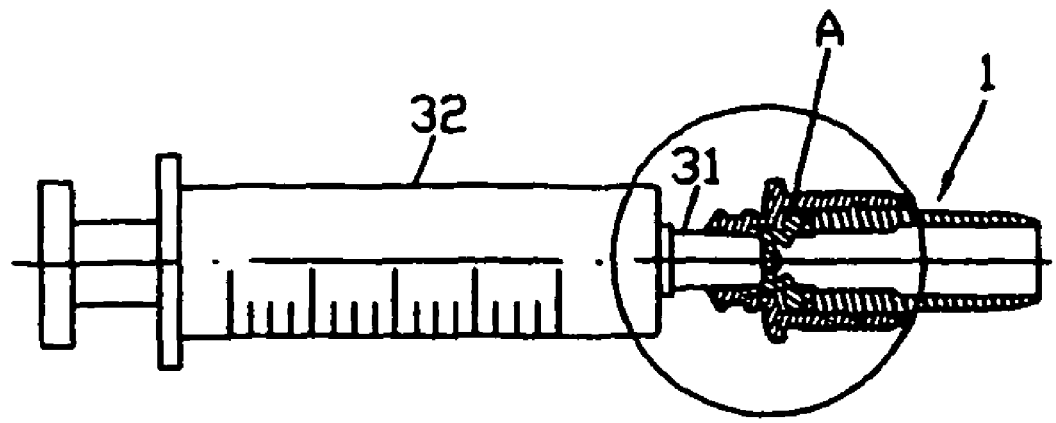
Figure 6B:
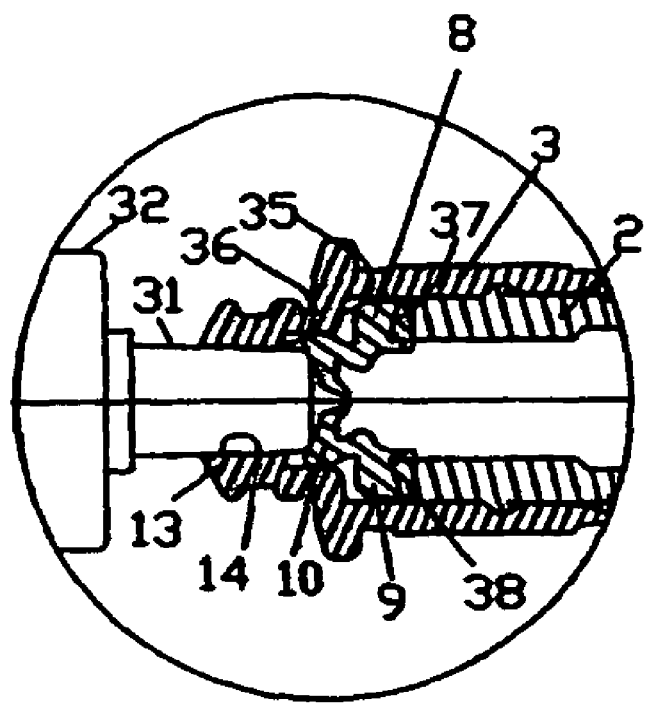

In the figures:

FIG. 1 shows a connector designed as an injection part for medical liquid-containing packages in side view, FIG. 2 shows a section through the connector from FIG. 1 along line A-A, FIG. 3 shows an infusion bag with the connector from FIG. 1, FIG. 4a shows a Luer syringe and a connector with broken-off break-off part, FIG. 4b shows detail A from FIG. 4a in a magnified view, FIG. 5a the Luer syringe and the connector from FIG. 4a during introduction of the conical shaft of the syringe into the connector, FIG. 5b shows detail A from FIG. 5a in a magnified view, FIG. 6a shows the Luer syringe and connector from FIG. 4a, whereby the conical shaft of the syringe is inserted into the connector and FIG. 6b shows detail A from FIG. 6a in a magnified view.

The connector according to the invention is designed as an injection part for the injection of an active substance into a package which contains a medical liquid, in particular an infusion or transfusion bag. Connector 20 has a connection part 1 with a channel-shaped recess 1c, which in the position of use comprises a lower section 2 on the package side and upper section 3 on the connection side. Connection part 1 therefore has an upper and lower opening 1a and 1b. The connector is an injection-moulded part made of polypropylene.

Lower section 2 of connection part 1 has a lower and upper cylindrical portion 4, 5, whereby the lower portion has a somewhat larger inner diameter than the upper portion, but a somewhat smaller outer diameter than the upper portion. Lower portion 4 can be pushed into a connecting sleeve of a film bag and welded or glued to the sleeve. It can however also be welded or glued directly into the film bag without a sleeve.

Upper section 3 of connection part 1 is fixed on lower section 2 in a snap-in fashion. For this purpose, the inner wall of the upper section has a peripheral groove 6, into which a peripheral projection 7 on the outer wall of upper section 3 snaps when the two sections are pressed together.

A self-sealing membrane 8 made of an elastic material, which is also referred to as a septum, is held clamped preferably with slight elastic deformation between lower and upper section 2, 3. Membrane 8 has an annular lower portion 9, which is clamped between upper and lower section 2, 3 of connection part 1. Lower annular portion 9 of membrane 8 is followed by a middle intermediate piece 34, which transforms into upper plate-shaped portion 10, which has a trough-shaped recess 11.

Connection part 1 has a lower and an upper shoulder 35, 36 projecting inwards. Annular portion 9 rests on lower shoulder 35 and plate-shaped portion 10 of membrane 8 rests on upper shoulder 36. The two portions 9, 10 of membrane 8 are preferably prestressed in a spring-like manner against shoulders 35, 36 of connection part 1. The inner diameter of annular portion 9 of membrane 8 is smaller than the inner diameter of channel-shaped recess 1c of connection part 1.

The membrane is provided with a continuous slit 12 in the centre of the plate-shaped portion. Membrane 10 can be provided with just a transverse-running slit or can also be slit in the shape of a cross or star. The slit preferably extends virtually over the whole cross-section of the plate-shaped portion. Trough-shaped recess 111 in plate-shaped portion 10 can have a curved or straight flank.

Above membrane 10, connection part 1 is designed as a connection piece 13, which has an internal cone 14 and preferably an external thread 15. The internal cone and external thread correspond to the conical shaft of the Luer lock connection of a conventional syringe, so that the conical shaft of the Luer lock syringe can be pushed in a sealing fashion into the internal cone of the connection piece and reliably screwed to the connection part. The external thread can also be dispensed with for the connection of a Luer syringe that does not have a screw connection.

Connection piece 13 is followed via an annular rupture zone 16 by a cap-shaped break-off part 17, which closes upper opening 1a of the connection piece. The break-off part forms an originality closure for the connector. Break-off part 17 has a lower rotationally symmetric base part 18 and an upper flat grip 19. Flat grip 19 is provided with a recess 21, which is formed in the manner of an arrow pointing downwards which identifies the connector as an injection part. To identify the flow direction, upper section 2 of the connection part also has a raised structure 22, which is formed in the manner of an arrow pointing downwards. Arrow 21 is arranged between projecting legs 23 which form a recessed grip.

FIG. 3 shows an infusion bag 30 together with injection part 20. Infusion bag 30 comprises two film layers 24, which are welded together at lower and upper edge 25 and longitudinal edges 26. A connecting sleeve 27 for injection part 20 and a connecting sleeve 28 for an extraction part 29 are welded into upper edge 25 of the infusion bag. Tubular connection part 1 of injection part 20 is pushed into connecting sleeve 27 and welded to the sleeve during sterilisation. The tubular connection part of the injection part can however also be moulded onto an insertion piece, which is round or designed in the manner of a boat and which is welded in between the two film layers.

For the injection of an active substance into the infusion solution, break-off part 17 of injection part 20 is twisted off or broken off by twisting or breaking the same, so that self-sealing membrane 8 lies free. Conical shaft 31 of a conventional Luer lock syringe 32 is pushed into internal cone 14 of connection piece 13, whereby the self-sealing membrane is pierced. The conical shaft of the syringe thereby provides a seal with respect to internal cone 14 of connection piece 13. Screw cap 33 of syringe 5 is then screwed onto external thread 5 of connection piece 17, so that the syringe is fixed to injection part 20. An active substance can then be injected by means of the syringe and the syringe again removed, whereby the membrane tightly closes the injection part.

Apart from the injection part, the infusion bag also has an extraction part 29 for extracting the infusion solution, which is welded to sleeve 28. The extraction part is however not the subject-matter of invention.

The mode of functioning of the self-sealing membrane is described in detail below.

Before the introduction of conical shaft 31 of a Luer syringe 32, annular and plate-shaped portions 9, 10 of membrane 8 rest on shoulders 35, 36 of connection part 1 (FIGS. 4a and 4b). When conical shaft 31 of syringe 32 is introduced, plate-shaped portion 10 of membrane 8 is compressed with deformation thereof (FIGS. 5a and 5b). Firstly plate-shaped portion 10 and then annular portion 9 of membrane 8 lose contact with shoulder 35 and 36 respectively. The plate-shaped portion of the membrane is thereby pressed against the wall of the connection part, so that the opening in the connection part is reliably sealed.

Internal cone 14 of connection piece 13 and self-sealing membrane 8 of connection part 1 are designed and arranged in such a way that conical shaft 31 of syringe 32 inserted into the internal cone opens slit membrane 8, but does not penetrate it (FIGS. 6a and 6b).

In order that spread-out membrane 8 is reliably held, the membrane is connected in a keyed manner to lower section 2 of connection part 1. For this purpose, membrane 8 has at the lower side a peripheral cutout 37, into which a peripheral projection 38 at the upper side of lower section 2 of connection part 1 engages.

The invention claimed is:

1. A connector for medical liquid-containing packages, in particular infusion or transfusion bags, comprising:
    a connection part, which has a channel-shaped recess in which a self-sealing membrane is arranged, whereby the channel-shaped recess has a package-side lower opening and a connection-side upper opening;
    a break-off part, which closes the channel-shaped recess and is connected to the connection part above the connection-side opening;
    wherein the connection part comprises a connection piece extending above the self-sealing membrane, whereby the self-sealing membrane is slit so as to receive the conical shaft of a syringe in a sealing fashion and wherein the connection piece and the self-sealing membrane of the connection part are designed and arranged in such a way that the conical shaft of a syringe inserted into the connection-side opening opens the slit membrane, but does not penetrate the slit of the self-sealing membrane.

2. The connector according to claim 1, wherein the connection piece of the connection part is designed as a female Luer connector with an internal cone.

3. The connector according to claim 2, wherein the Luer connector of the connection part is designed as a female Luer lock connector with an internal cone and an external thread.

4. The connector according to claim 1, wherein the break-off part is connected via an annular rupture zone to the connection part.

5. The connector according to claim 1, wherein the connection part comprises a lower section and an upper section, whereby the sections are fixed in a snap-in fashion.

6. The connector according to claim 5, wherein the self-sealing membrane is held clamped between the lower and upper section.

7. The connector according to claim 1, wherein the self-sealing membrane has a lower annular portion and an upper plate-shaped portion, which has a mould-shaped recess.

8. The connector according to claim 7, wherein the upper plate-shaped portion is followed by a middle intermediate piece, which transforms into the lower annular portion of the self-sealing membrane.

9. The connector according to claim 7, wherein the annular portion of the self-sealing membrane is clamped between the lower and upper section of the connection part.

10. The connector according to claim 7, wherein the connection part has a shoulder projecting inwards, on which the annular portion of the self-sealing membrane rests.

11. The connector according to claim 7, wherein the connection part has a shoulder projecting inwards, on which the plate-shaped portion of the self-sealing membrane rests.

12. The connector according to claim 11, wherein the plate-shaped portion of the self-sealing membrane is prestressed in a spring-like manner against the shoulder projecting inwards.

13. The connector according to claim 7, wherein the annular portion of the self-sealing membrane is connected in a keyed manner to the lower section of the connection part.

14. The connector according to claim 7, wherein the inner diameter of the annular portion of the self-sealing membrane is smaller than the inner diameter of the channel-shaped recess of the connection part.

15. The connector according to claim 1, wherein the break-off part is designed as a flat grip.

16. A package for medical liquids, in particular infusion or transfusion bags, with a connector according to claim 1.

17. A connector for medical liquid-containing packages, in particular infusion or transfusion bags, comprising:
    a connection part, which has a channel-shaped recess in which a self-sealing membrane is arranged, whereby the channel-shaped recess has a package-side lower opening and a connection-side upper opening;
    a break-off part, which closes the channel-shaped recess and is connected to the connection part above the connection-side opening;
    wherein the connection part comprises a connection piece having an internal cone and extending above the self-sealing membrane, whereby the self-sealing membrane is slit so as to receive the conical shaft of a syringe in a sealing fashion.

* * * * *